United States Patent
Nackaerts et al.

(10) Patent No.: US 9,739,774 B2
(45) Date of Patent: Aug. 22, 2017

(54) SUBSTANCE DETECTION DEVICE

(71) Applicant: NXP B.V., Eindhoven (NL)

(72) Inventors: Axel Nackaerts, Leuven (BE); Viet Hoang Nguyen, Leuven (NL)

(73) Assignee: NXP B.V., Eindhoven (NL)

( * ) Notice: Subject to any disclaimer, the term of this patent is extended or adjusted under 35 U.S.C. 154(b) by 0 days.

(21) Appl. No.: 14/845,166

(22) Filed: Sep. 3, 2015

(65) Prior Publication Data

US 2017/0067891 A1   Mar. 9, 2017

(51) Int. Cl.
| | |
|---|---|
| *G01N 27/00* | (2006.01) |
| *G01N 33/48* | (2006.01) |
| *G01N 33/558* | (2006.01) |
| *G01N 27/22* | (2006.01) |
| *G01N 33/543* | (2006.01) |
| *G01N 33/68* | (2006.01) |

(52) U.S. Cl.
CPC ......... *G01N 33/558* (2013.01); *G01N 27/227* (2013.01); *G01N 33/5438* (2013.01); *G01N 33/689* (2013.01)

(58) Field of Classification Search
CPC .............................. G01N 27/00; G01N 33/48
USPC .................... 422/50, 68.1, 82.01; 436/43, 65
See application file for complete search history.

(56) References Cited

U.S. PATENT DOCUMENTS

| | | | |
|---|---|---|---|
| 5,580,794 A | 12/1996 | Allen | |
| 5,958,791 A | 9/1999 | Roberts et al. | |
| 6,194,224 B1 | 2/2001 | Good et al. | |
| 6,358,752 B1 | 3/2002 | Durst et al. | |
| 6,485,938 B1 | 11/2002 | Sheppard et al. | |
| 7,834,646 B2 | 11/2010 | Chambon et al. | |
| 2003/0098233 A1 | 5/2003 | Kermani et al. | |
| 2003/0180815 A1 | 9/2003 | Rawson et al. | |
| 2005/0239216 A1 | 10/2005 | Feistel | |
| 2006/0281193 A1 | 12/2006 | Petrilla et al. | |
| 2010/0062414 A1 | 3/2010 | Yamamoto et al. | |

(Continued)

FOREIGN PATENT DOCUMENTS

| | | |
|---|---|---|
| CN | 1791796 A | 6/2006 |
| EP | 2508874 A1 | 10/2012 |

(Continued)

OTHER PUBLICATIONS

Counterpart of application No. CN201280060417.6; 7 pages; (Feb. 9, 2015).

(Continued)

*Primary Examiner* — Brian J Sines (57) ABSTRACT

One example discloses a substance detection device, including: a substrate configured to carry a substance; wherein the substrate has a length and a substance loss along the length of the substrate; a test region coupled to the substrate and configured to bond to at least a portion of the substance; a sensor coupled to the substrate at a fixed location along the length and having a sensing signal output; an integration circuit coupled to the sensor and configured to integrate, over a time interval, a signal from the sensing signal output; and a detection circuit coupled to the integration circuit and configured to output a substance detected signal if the integrated sensing signal output signal deviates from the substance loss corresponding to the fixed sensor location.

16 Claims, 9 Drawing Sheets

(56) References Cited

U.S. PATENT DOCUMENTS

| | | |
|---|---|---|
| 2010/0274181 A1 | 10/2010 | Wang et al. |
| 2011/0053289 A1 | 3/2011 | Lowe et al. |
| 2011/0186428 A1 | 8/2011 | Beaty et al. |
| 2011/0208435 A1 | 8/2011 | Elder et al. |
| 2012/0073986 A1 | 3/2012 | Jackson et al. |
| 2014/0273054 A1* | 9/2014 | Franciskovich ....... G01N 33/52 |
| | | 435/26 |

FOREIGN PATENT DOCUMENTS

| | | |
|---|---|---|
| JP | 2010286261 A | 12/2010 |
| WO | 02/10754 A2 | 2/2002 |
| WO | 2004/010143 A2 | 1/2004 |
| WO | 2006/010072 A2 | 1/2006 |
| WO | 2008/040983 A1 | 4/2008 |
| WO | 2009/144507 A1 | 5/2009 |

OTHER PUBLICATIONS

International Search Report for Application No. PCT/EP2012/074624; 12 pages (Jan. 25, 2013).
Office Action U.S. Appl. No. 14/363,449; 16 pages (Jun. 22, 2016).
Extended European Search Report for Patent Appln. No. 16183667.1 (Dec. 5, 2016) 7 pages.
Final OA for U.S. Appl. No. 14/363,449; 24 pages (Oct. 18, 2016).
NFOA for U.S. Appl No. 14/363,449; 17 pages (Feb. 22, 2017).

* cited by examiner

SUBSTANCE DETECTION DEVICE

The present specification relates to systems, methods, apparatuses, devices, articles of manufacture and instructions for substance detection.

In a lateral flow test, an analyte fluid containing the nanoparticles move through a porous membrane (e.g. test strip, substrate, etc.), except when passing the test and control lines/regions on the test strip, where a subset of the particles are captured and retained. Optical lateral flow sensing is often used for pregnancy testing; however, optical techniques suffer from either a high bill-of-materials cost or low quantitative accuracy.

INCORPORATION BY REFERENCE UNDER 37CFR§1.57

The specification herein incorporates by reference U.S. patent application Publication Ser. No. 14/363,449, publication number 20140323350 published on Oct. 30, 2014.

SUMMARY

According to an example embodiment, a substance detection device, comprising: a substrate configured to carry a substance; wherein the substrate has a length and a substance loss along the length of the substrate; a test region coupled to the substrate and configured to bond to at least a portion of the substance; a sensor coupled to the substrate at a fixed location along the length and having a sensing signal output; an integration circuit coupled to the sensor and configured to integrate, over a time interval, a signal from the sensing signal output; and a detection circuit coupled to the integration circuit and configured to output a substance detected signal if the integrated sensing signal output signal deviates from the substance loss corresponding to the fixed sensor location.

In another example embodiment, the detection circuit is configured to output the substance detected signal if the integrated sensing signal output signal is either greater than or less than the substance loss corresponding to the fixed sensor location.

In another example embodiment, the substance loss is either a uniform per unit length or variable substance loss.

In another example embodiment, at the fixed location along the length, the test region is not located directly over the sensor.

In another example embodiment, the sensor is a capacitive sensor.

In another example embodiment, the substance is at least one of: a target molecule; a control molecule; a conjugate molecule, a particle, DNA, a protein, an enzyme, a peptide, a small molecules or a hormone.

In another example embodiment, the substance is carried by at least one of: an analyte or biological fluid.

In another example embodiment, the test region includes at least one of: an antibody, a sensitive region, or a biomarker.

In another example embodiment, the substance detected signal is a pregnancy detected signal.

In another example embodiment, the sensor is included in a set of sensors 106, each having a sensing signal output, and aligned in a row along the length of the substrate at a corresponding set of fixed sensor locations; the integration circuit is coupled to the set of sensors and is configured to integrate, over the time interval, signals from the sensing signal outputs; and the detection circuit is configured to output the substance detected signal if at least one of the integrated sensing signal output signals deviates from a corresponding substance loss at that fixed sensor location.

In another example embodiment, the substrate is a membrane having a porosity between 66% and 98% by volume.

In another example embodiment, the sensor includes a set of electrodes separated from the substrate by an electrical insulator.

In another example embodiment, the sensor is included in a set of sensors, each having a sensing signal output, and aligned in a row along the length of the substrate at a corresponding set of fixed sensor locations; and further comprising a substance loss circuit configured to compare the set of sensing signal outputs to calculate the substance loss.

In another example embodiment, the sensor is included in a set of sensors, each having a sensing signal output, and aligned in a row along the length of the substrate at a corresponding set of fixed sensor locations; and further comprising a flow rate circuit configured to determine a volume flow rate along the substrate by comparing the set of sensing signal outputs.

In another example embodiment, the substrate configured to carry a second substance; the substrate has a second substance loss with respect to the second substance; further comprising, a control region coupled to the substrate and configured to bond to at least a portion of the second substance; and a second sensor coupled to the substrate at a second fixed location along the length and having a second sensing signal output; the integration circuit is coupled to the second sensor and is configured to integrate, over a time interval, a signal from the second sensing signal output; and the detection circuit is configured to output a second substance detected signal if the second integrated sensing signal output signal deviates from a second substance loss corresponding to the second fixed sensor location.

According to another example embodiment, a pregnancy test device comprising: a substrate configured to carry a substance; the substrate has a length and a substance loss along the length of the substrate; a test region coupled to the substrate and configured to bond to at least a portion of the substance; a sensor coupled to the substrate at a fixed location along the length and having a sensing signal output; an integration circuit coupled to the sensor and configured to integrate, over a time interval, a signal from the sensing signal output; and a detection circuit coupled to the integration circuit and configured to output a pregnancy detected signal if the integrated sensing signal output signal deviates from the substance loss corresponding to the fixed sensor location.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

A substance detection device is discussed herein. One example of this device uses several electrodes in a row on a substrate (e.g. a test strip, membrane, etc.) to dynamically sense a total amount of a substance (e.g. biological fluid, nanoparticle, molecule, etc.) flowing laterally past one or more sensors (e.g. capacitive electrodes) along the substrate. The sensor readings are time-integrated (i.e. area under the curve), thus it is possible to detect substance bonding to a test region (e.g. a pregnancy antibody test line) by monitoring a divergence of a sensor reading from either a calculated or measure substrate loss.

If more than one sensor, the sensor readings can be compared to calculate an amount of a substance (e.g. nanoparticles) retained at a test region or flowing by (e.g. functioning as a flow-rate sensor)

Example embodiments of the substance detection device's design relaxes requirements for accurate placement of the test region and/or an optional control region 110 (e.g. another molecularly reactive molecule) relative to a set of sensing elements.

Figure 1A:
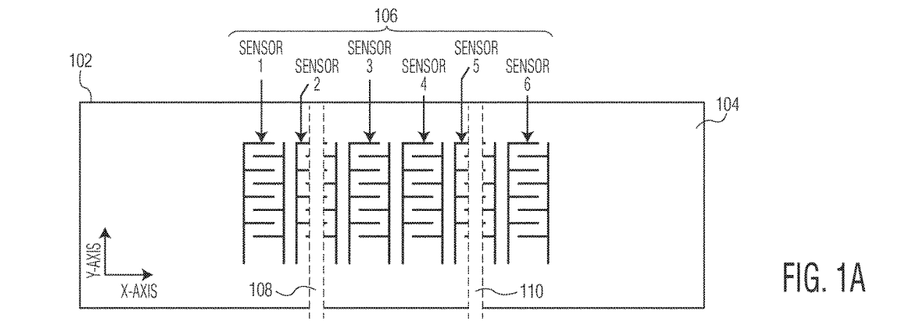
FIG. 1A is an example substance detection device.

FIG. 1A is an example substance detection device 102. The device 102 includes a substrate 104, a set of sensors 106, a test region 108, and a control region 110. The substance detection device 102 is coupled to an integration circuit (not shown), a detection circuit (not shown), a substance loss circuit (not shown), and a flow rate circuit (not shown).

The substrate 104 in various examples can be a membrane, a test strip, or another particle carrying structure. The substrate 104 has a length along the x-axis and a substance loss along the length of the substrate 104. In one example the substrate 104 is a membrane having a porosity between 66% and 98% by volume. The substrate 104 is configured to carry a substance.

The substance (not shown) can be at least one of or a combination of: a target molecule; a control molecule; a conjugate molecule, a particle, DNA, a protein, an enzyme, a peptide, a small molecules, a hormone, or a pregnancy related molecule. In one example, the substance can be carried by an analyte, biological fluid or some other mechanical, chemical, electrical or bio-molecular process. In another example, the substance is a mixture including a carrier (e.g. including an analyte, biological fluid, etc.)

The set of sensors 106 (e.g. sensors 1, 2, 3, 4, 5, 6) are sensitive to the substance. In one example the sensors 106 are capacitive sensors. The sensors 106, each having a sensing signal output, are aligned in a row along the length of the substrate 104 (e.g. along the x-axis) at a corresponding set of fixed sensor locations (as shown in FIG. 1). The sensors 106 each include a set of electrodes (e.g. each terminal of an interdigitated capacitive structure) which are in one example separated from the substrate 104 by an electrical insulator (e.g. flex-foil). In one example the sensors 106 are equidistantly separated, however in another example the sensors 106 are variably located along the x-axis of the substrate 104.

The test region 108 (e.g. test line) is coupled to the substrate 104 and configured to bond to at least a portion of the substance. For proper bonding the test region 108 may include at least one of: an antibody, a sensitive region, or a biomarker. In one example embodiment, substance-A attaches to analyte-A and the combination of the substance-A and the analyte-A attach to the test region 108.

The integration circuit (not shown) is electrically coupled to the sensor 106 and is configured to integrate, over a time interval, one or more signals from the sensor's 106 sensing signal outputs.

Figure 2:
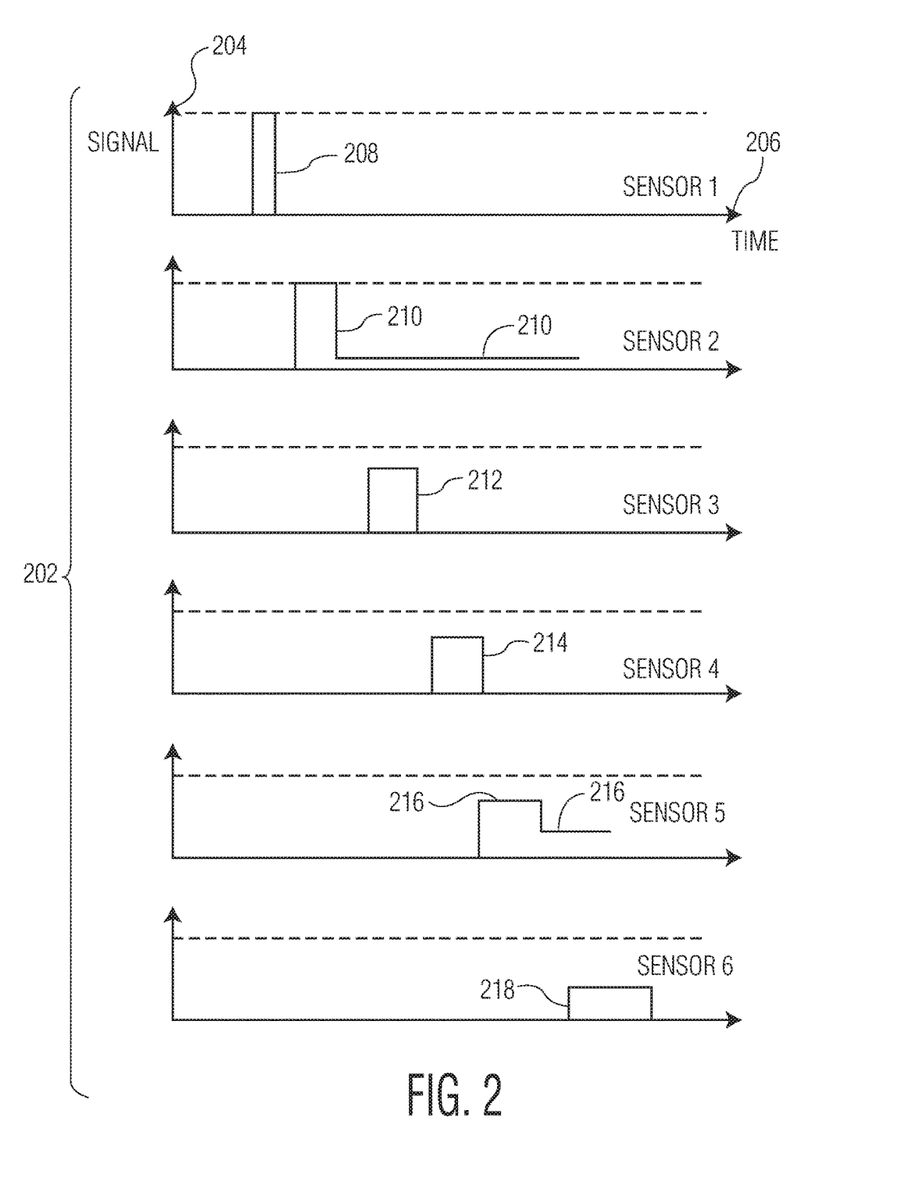
FIG. 2 is an example set of sensor output signals in response to a substance flow through the substance detection device.

FIG. 2 is an example set of sensor output signals 208, 210, 212, 214, 216, 218 in response to a substance flow through the substance detection device 102. A set of sensor outputs 202 are shown each having a signal strength 204 over time 206. Signal strength 204 peaks get wider and lower at successive sensors (e.g. sensors 2, 3, 4, 5, 6) due to: substance diffusion, substance retention by bonding at the test region 108 and control region 110, and substance transport losses within the substrate 104.

The detection circuit (not shown) is coupled to the integration circuit and configured to output a substance detected signal if at least one of the integrated sensing signal output signals deviates from a corresponding substance loss expected at the location of the sensor that detected the deviation.

Figure 3:
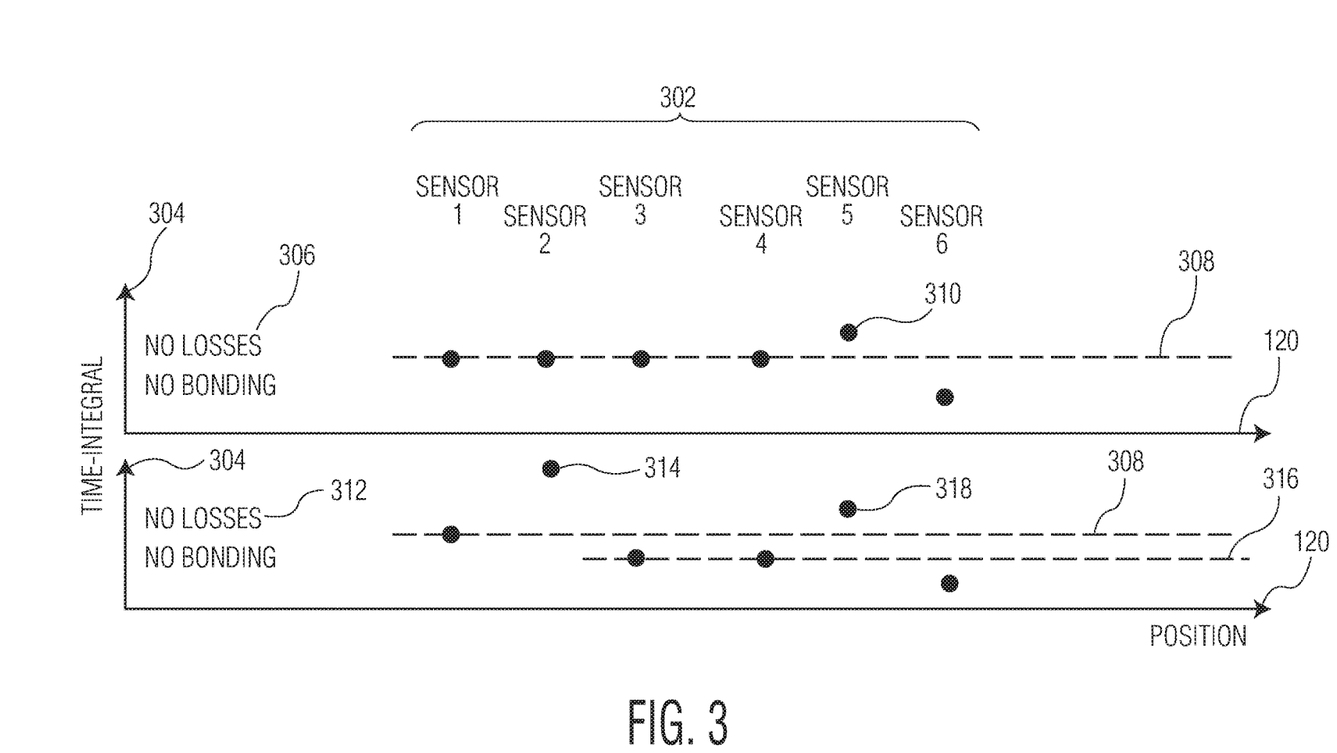
FIG. 3 is an example set of time integrated, no loss, sensor output signals in response to the substance flow through the substance detection device.
Figure 4:
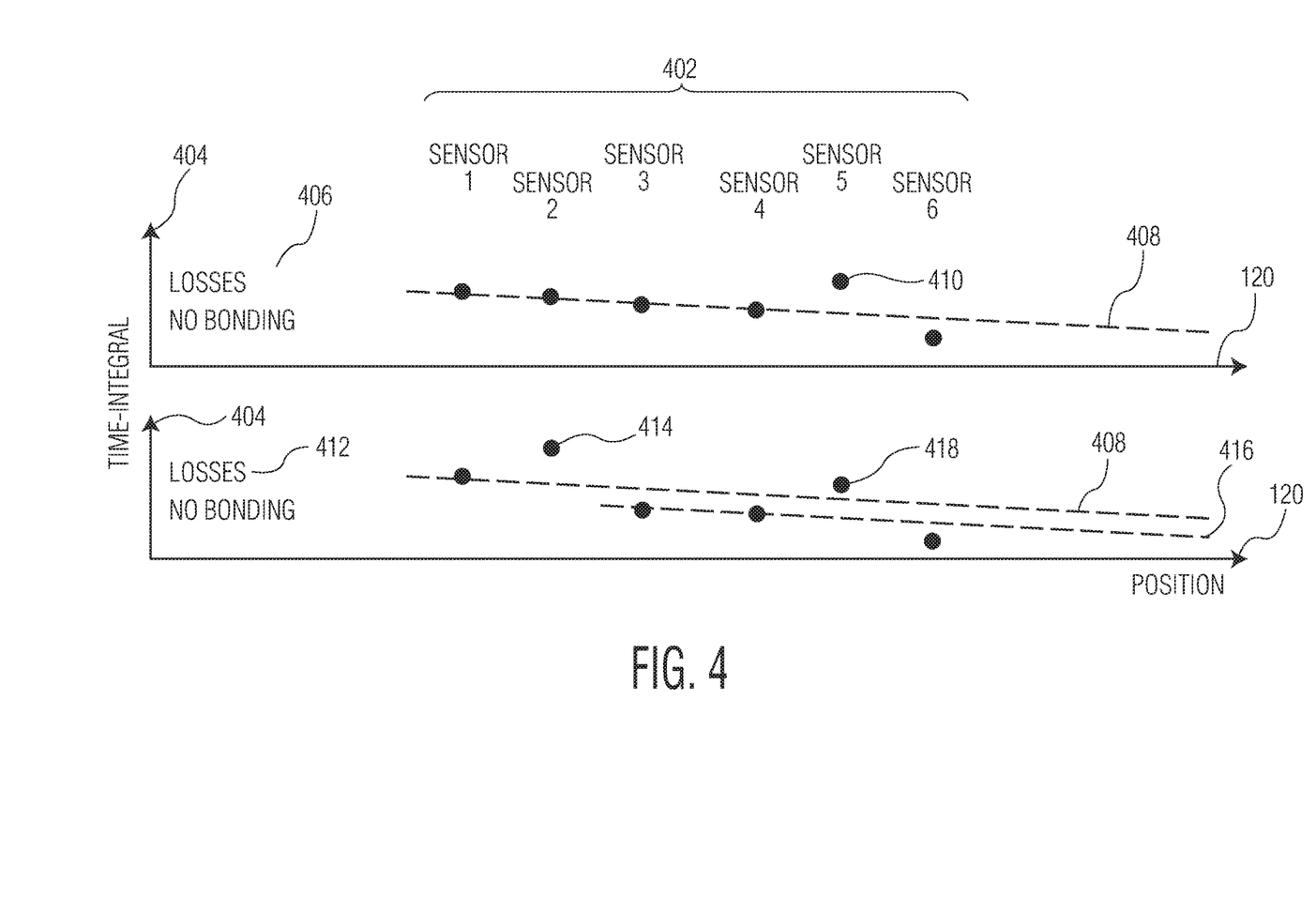
FIG. 4 is an example set of time integrated lossy sensor output signals in response to the substance flow through the substance detection device.

FIGS. 3 and 4 show example sets of time integrated sensor output signals 208, 210, 212, 214, 216, 218 in response to the substance flow through the substance detection device 102. The time integrated values are shown as "dots". Deviations 310, 314 and 318 from the substrate's 104 substance loss 308, 316 are also shown and will be discussed further below.

The substance loss circuit (not shown) is configured to compare a set of sensor output signals 208, 210, 212, 214, 216, 218 to calculate the substance loss for the substrate 104. In another example, the substance loss is based on an earlier set of substrate 104 characterization data produced by a substrate manufacturer.

The flow rate circuit (not shown) is configured to determine a volume flow rate along the substrate 104 by comparing a timing of the set of sensor output signals 208, 210, 212, 214, 216, 218. For example, a leading edge of each of the sensor output signals 208, 210, 212, 214, 216, 218 can be compared to determine how fast the substance is flowing through the substrate 104.

The control region 110 (e.g. control line) is optional, and in one example is only used to determine that a second substance is flowing through the substrate 104. For example the second substance may just be an analyte chemical that does not relate to the substance detection device's 102 primary substance detection purpose. In another example, the control region 110 is instead a second test region that does relate to the substance detection device's 102 primary substance detection purposes.

Thus in this example, the substrate 104 configured to carry the second substance, and the substrate 104 has a second substance loss with respect to the second substance. The control region 110 is coupled to the substrate 104 and configured to bond to at least a portion of the second substance. Thus for example, a second substance-B attaches to a second analyte-B and second analyte-B attaches to the control region 110.

A second sensor (e.g. sensors 2, 3, 4, 5 or 6) is coupled to the substrate 104 at a second fixed location along the length and has a second sensing signal output. The integration circuit is coupled to the second sensor and is configured to integrate, over a time interval, a signal from the second sensing signal output. The detection circuit is configured to output a second substance detected signal if the second integrated sensing signal output signal deviates from a second substance loss corresponding to the second fixed sensor location.

Figure 1B:
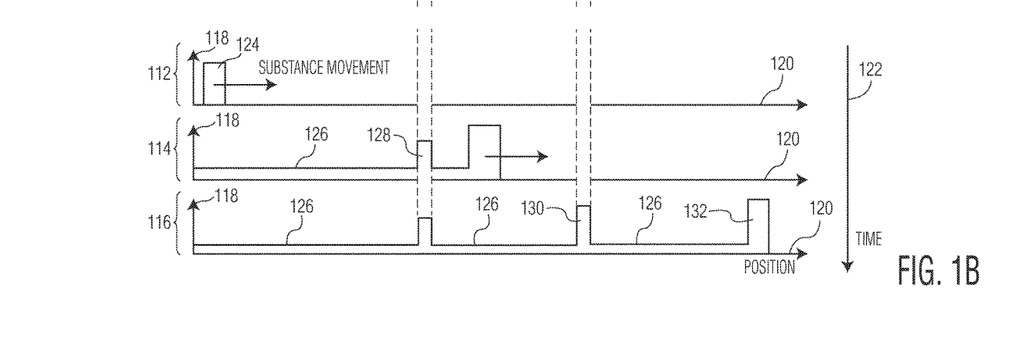
FIG. 1B is an example substance flow through the substance detection device.

FIG. 1B is an example substance flow through the substance detection device 102. An evolution in time of substance concentration over the length of the substrate 104 is shown, as well s bonding at both the test region 108 and control region 110. Three axis are shown: substance concentration level 118, position 120 along length of the substrate 104, and time 122.

A first substance distribution 112 at a first time 122, a second substance distribution 114 at a second time 122, and a third substance distribution 116 at a third time 122 are shown. An initial mixture concentration 124 is added to the substrate 104 as shown in the first substance distribution 112. The mixture in this example includes at least two substances.

From the first time 122 to the second time 122 the mixture diffuses through the substrate 104. A per unit length substance loss 126 for the substances is shown in the second substance distribution 114. Also show in the second substance distribution 114 is a bonding of a first substance 128 at test region 108.

From the second time 122 to the third time 122 the mixture diffuses further through the substrate 104 as shown in the third substance distribution 116. The per unit length substance loss 126 continues and a bonding of a second substance 130 at control region 110 now appears. Additional per unit length substance losses 126 and a final mixture concentration 132 are also shown in the third substance distribution 116.

FIG. 3 is an example set of time integrated, no loss, sensor output signals in response to the substance flow through the substance detection device 102. No loss here refers to a lack of substance losses along the substrate 104, as shown by the flat first substrate loss slope 308 and second substrate loss slope 316. A set of integrated sensor signals 302 are shown as "dots" in a graph having a time integral 304 y-axis value over a substrate position 120 x-axis value. These "dots" represent a quantity (e.g. area under the curve) of the substance (e.g. nanoparticles) that passed over the sensors 106.

First shown is an example having no losses and no test region bonding 306. Integrated sensor output signals from sensors 1, 2, 3, 4 are all equal, since the substrate 104 does not have losses which errantly capture the substance. This flat line defines the first substrate loss slope 308.

However sensor 5's integrated value has deviated from the first substrate loss slope 308. The detection circuit interprets this as a control region deviation 310 since sensor 5 is located at the control region 110 in FIG. 1A. Sensor 6's integrated value drops below the first substrate loss slope 308 since after the substance's bonding to the control region 110 a new baseline substrate loss slope has been created.

Second shown is an example having no losses but with test region bonding 312. Integrated sensor output signals from sensor 1 is at the first substrate loss slope 308. Then Sensor 2's integrated value has deviated from the first substrate loss slope 308. The detection circuit interprets this as a test region deviation 314 since sensor 2 is located at the test region 108 in FIG. 1A. Sensor 3's integrated value drops below the first substrate loss slope 308 since after the substance's bonding to the test region 108 a new second substrate loss slope 316 has been created.

Integrated sensor output signals from sensors 3 and 4 are at the second substrate loss slope 316. Then Sensor 5's integrated value has deviated from the second substrate loss slope 316. The detection circuit interprets this as a control region deviation 318 since sensor 5 is located at the control region 110 in FIG. 1A. Sensor 6's integrated value drops below the second substrate loss slope 316 since after the substance's bonding to the control region 110 a new baseline substrate loss slope has been created.

FIG. 4 is an example set of time integrated lossy sensor output signals in response to the substance flow through the substance detection device 102. Loss here refers to substance losses along the substrate 104, as shown by the sloped first substrate loss slope 408 and second substrate loss slope 416. The substance loss in one example is a uniform per unit length loss, or in another a variable (i.e. non-uniform) substance loss. A set of integrated sensor signals 402 are shown as "dots" in a graph having a time integral 404 y-axis value over a substrate position 120 x-axis value.

First shown is an example having losses but without test region bonding 406. Integrated sensor output signals from sensors 1, 2, 3, 4 are all following the predicted or calculated first substrate loss slope 408.

However sensor 5's integrated value has deviated from (i.e. is greater than) the first substrate loss slope 408. The detection circuit interprets this as a control region deviation 410 since sensor 5 is located at the control region 110 in FIG. 1A. Sensor 6's integrated value drops below the first substrate loss slope 408 since after the substance's bonding to the control region 110 a new baseline substrate loss slope has been created.

Second shown is an example having losses and test region bonding 412. Integrated sensor output signals from sensor 1 is at the first substrate loss slope 408. Then Sensor 2's integrated value has deviated from (i.e. is greater than) the first substrate loss slope 408. The detection circuit interprets this as a test region deviation 414 since sensor 2 is located at the test region 108 in FIG. 1A. Sensor 3's integrated value drops below the first substrate loss slope 408 since after the substance's bonding to the test region 108 a new second substrate loss slope 416 has been created.

Integrated sensor output signals from sensors 3 and 4 are at the second substrate loss slope 416. Then Sensor 5's integrated value has deviated from (i.e. is greater than) the second substrate loss slope 416. The detection circuit interprets this as a control region deviation 418 since sensor 5 is located at the control region 110 in FIG. 1A. Sensor 6's integrated value drops below the second substrate loss slope 416 since after the substance's bonding to the control region 110 a new baseline substrate loss slope has been created.

Figure 5A:
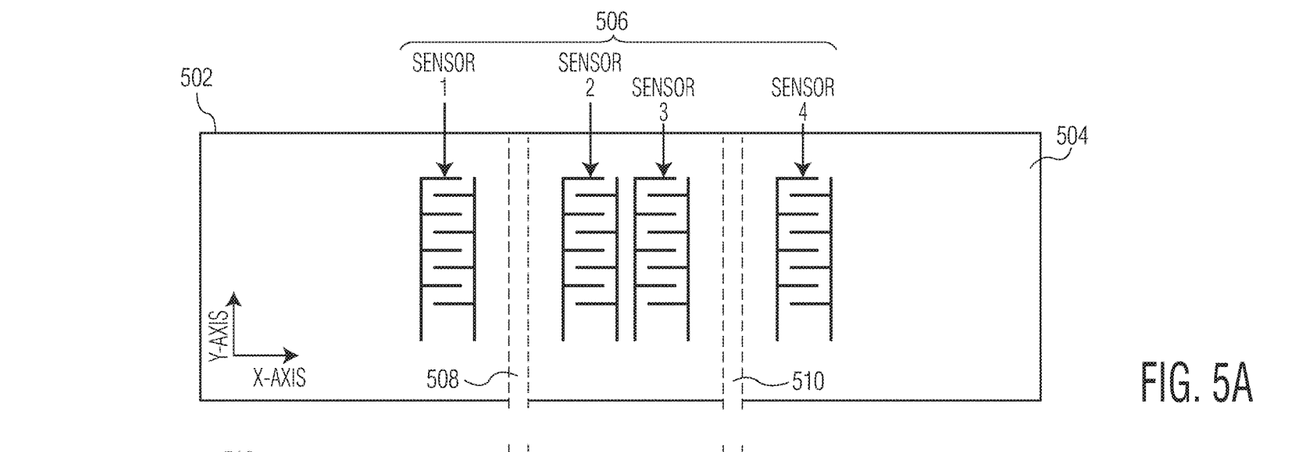
FIG. 5A is an example second substance detection device.

FIG. 5A is an example second substance detection device 502. The device 502 includes a substrate 504, a set of sensors 506, a test region 508, and a control region 510. The substance detection device 502 is also coupled to an integration circuit (not shown), a detection circuit (not shown), a substance loss circuit (not shown), and a flow rate circuit (not shown).

The set of sensors 506 (e.g. sensors 1, 2, 3, 4) are sensitive to a substance. The test region 508 (e.g. test line) is coupled to the substrate 504 and configured to bond to at least a portion of the substance. In this example, the test region 508 and control region 510 are not located directly over the sensors 506. The effect of this dislocation on the integrated sensor output signals and their interpretation by the detection circuit is discussed further with respect to FIG. 6.

Figure 5B:
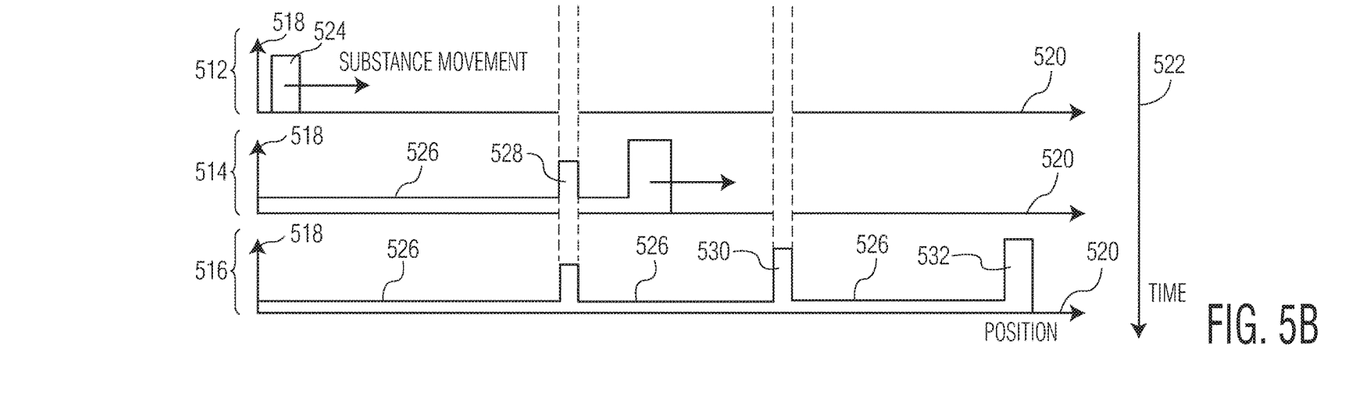
FIG. 5B is an example substance flow through the second substance detection device.

FIG. 5B is an example substance flow through the second substance detection device 502. In this example, the evolution in time of substance concentration over the length of the substrate 504 as well as bonding at both the test region 508 and control region 510 is substantially similar to FIG. 1B. Three axis are shown: substance concentration level 518, position 520 along length of the substrate 504, and time 522.

A first substance distribution 512 at a first time 522, a second substance distribution 514 at a second time 522, and a third substance distribution 516 at a third time 522 are shown. An initial mixture concentration 524 is added to the substrate 504 as shown in the first substance distribution 512. The mixture in this example includes at least two substances.

From the first time 522 to the second time 522 the mixture diffuses through the substrate 504. A per unit length substance loss 526 for the substances is shown in the second substance distribution 514. Also show in the second substance distribution 514 is a bonding of a first substance 528 at test region 508.

From the second time 522 to the third time 522 the mixture diffuses further through the substrate 504 as shown in the third substance distribution 516. The per unit length substance loss 526 continues and a bonding of a second substance 530 at control region 510 now appears. Additional per unit length substance losses 526 and a final mixture concentration 532 are also shown in the third substance distribution 516.

Figure 6:
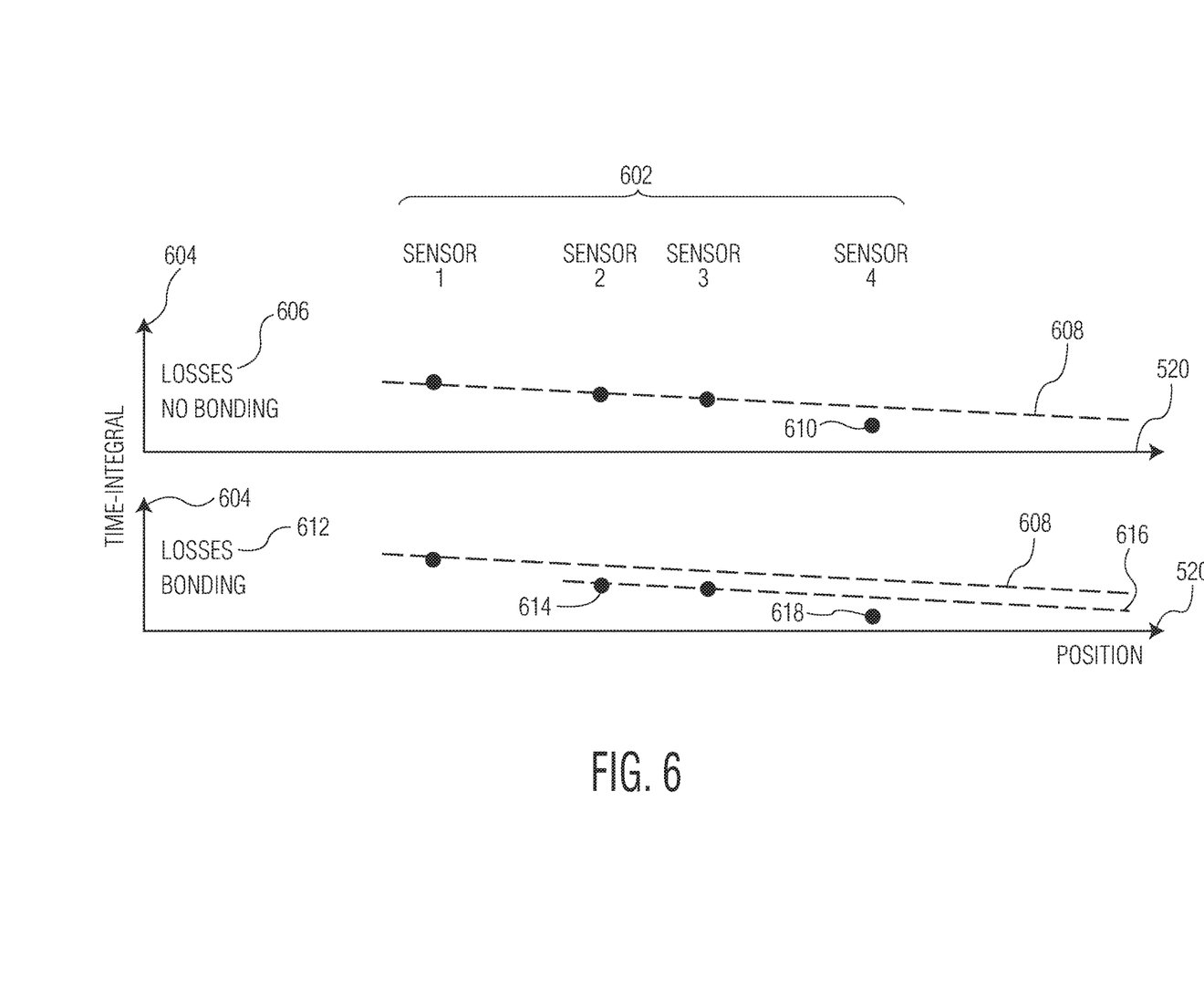
FIG. 6 is an example set of time integrated lossy sensor output signals in response to the substance flow through the second substance detection device.

FIG. 6 is an example set of time integrated lossy sensor output signals in response to the substance flow through the second substance detection device 502. Loss here refers to substance losses along the substrate 504, as shown by the sloped first substrate loss slope 608 and second substrate loss slope 616. A set of integrated sensor signals 602 are shown as "dots" in a graph having a time integral 604 y-axis value over a substrate position 520 x-axis value.

First shown is an example having losses but without test region bonding 606. Integrated sensor output signals from sensors 1, 2, 3 are all following the predicted or calculated first substrate loss slope 608.

However sensor 4's integrated value has deviated from (i.e. is less than) the first substrate loss slope 608. The detection circuit interprets this as a control region deviation 610 since sensor 4 is located somewhere after the control region 510 in FIG. 5A.

Second shown is an example having losses and test region bonding 612. Integrated sensor output signals from sensor 1 is at the first substrate loss slope 608. Then Sensor 2's integrated value has deviated from (i.e. is less than) the first substrate loss slope 608. The detection circuit interprets this as a test region deviation 614 since sensor 2 is located somewhere after the test region 508 but somewhere before the control region 510 in FIG. 5A. Sensor 2's integrated value drops below the first substrate loss slope 608 since after the substance's bonding to the test region 508 a new second substrate loss slope 616 has been created.

Integrated sensor output signal from sensor 3 is also at the second substrate loss slope 616. Then Sensor 4's integrated value has deviated from (i.e. is less than) the second substrate loss slope 616. The detection circuit interprets this as a control region deviation 618 since sensor 4 is located somewhere after the control region 510 in FIG. 5A.

Viewing the examples in FIGS. 4 and 6, the detection circuit in one example is configured to output the substance detected signal if the integrated sensing signal output signal is either greater than or less than the substance loss corresponding to the fixed sensor location. Thus any deviation from the first or second slopes 608, 616 in the graphs are a quantitative measure for the bonding in the test regions 108, 508 and control regions 110, 510, even if the test regions 108, 508 and control regions 110, 510 are not on top of the sensors 106, 506.

Figure 7:
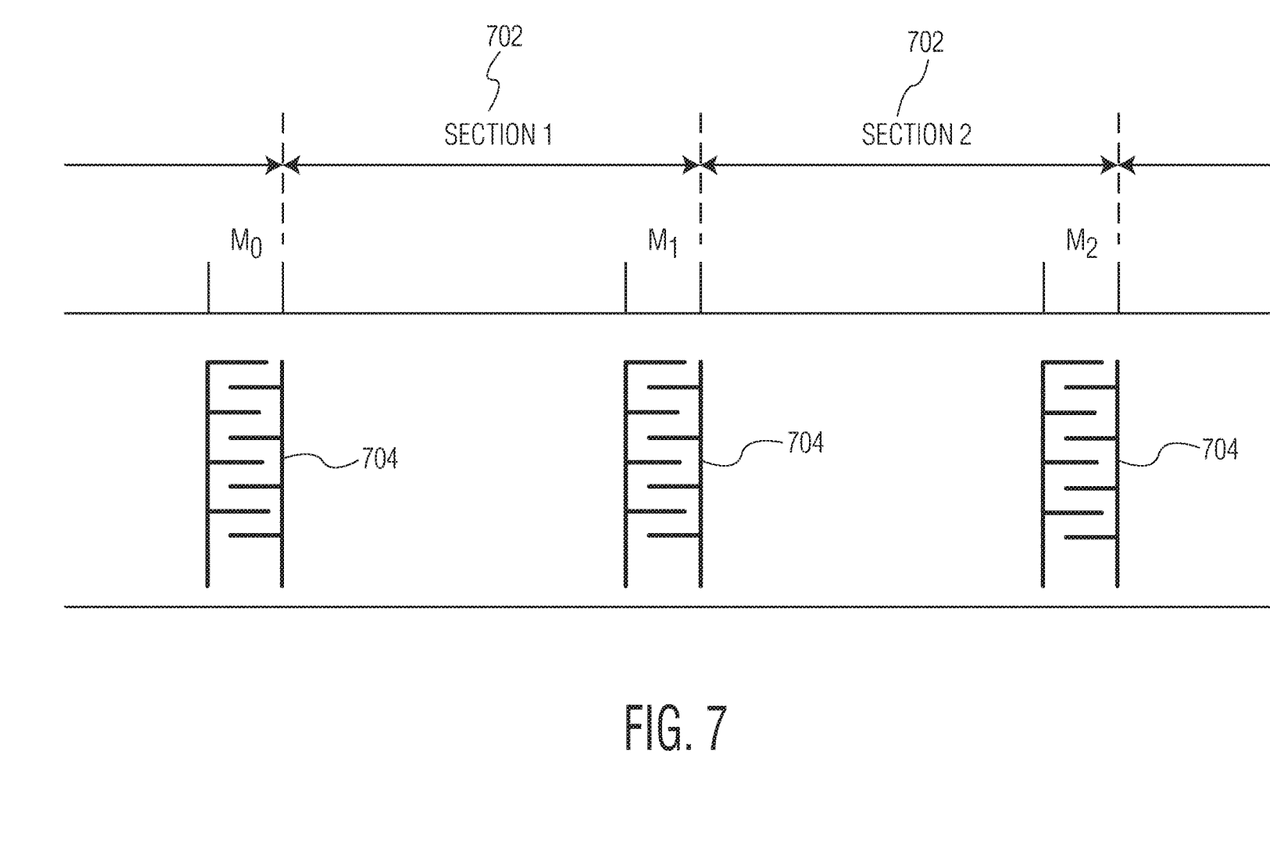
FIGS. 7, 8 and 9 present an example set of substance detection device elements configured to detect a substance based on a set of sensor output signals.
Figure 8A:
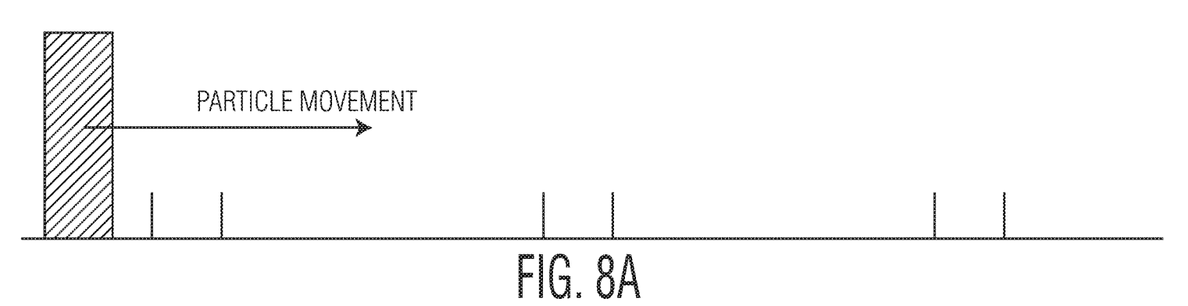
Figure 8B:
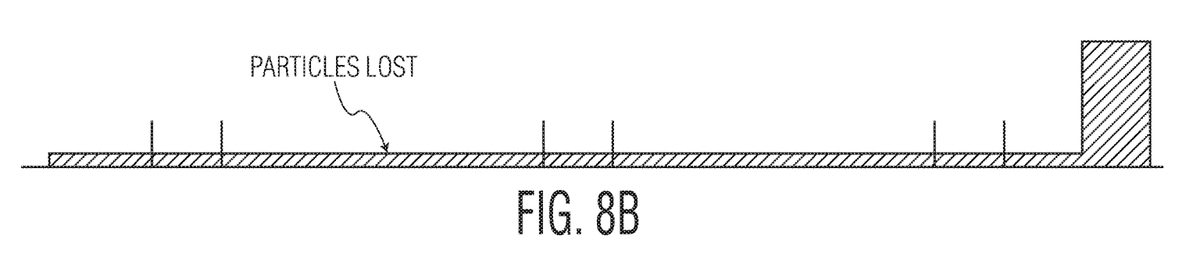
Figure 8C:
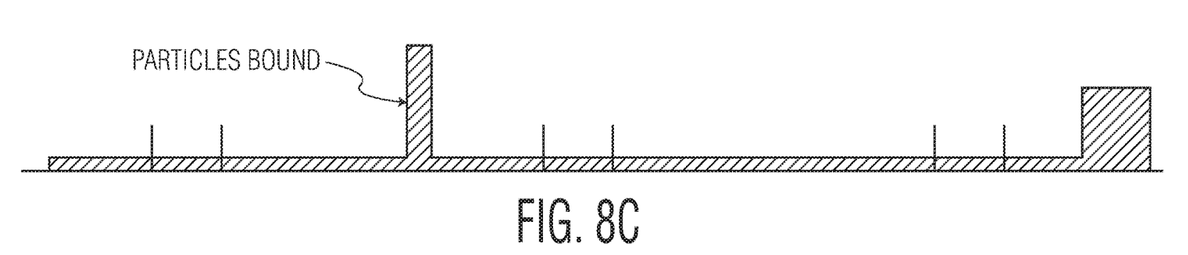
Figure 9:
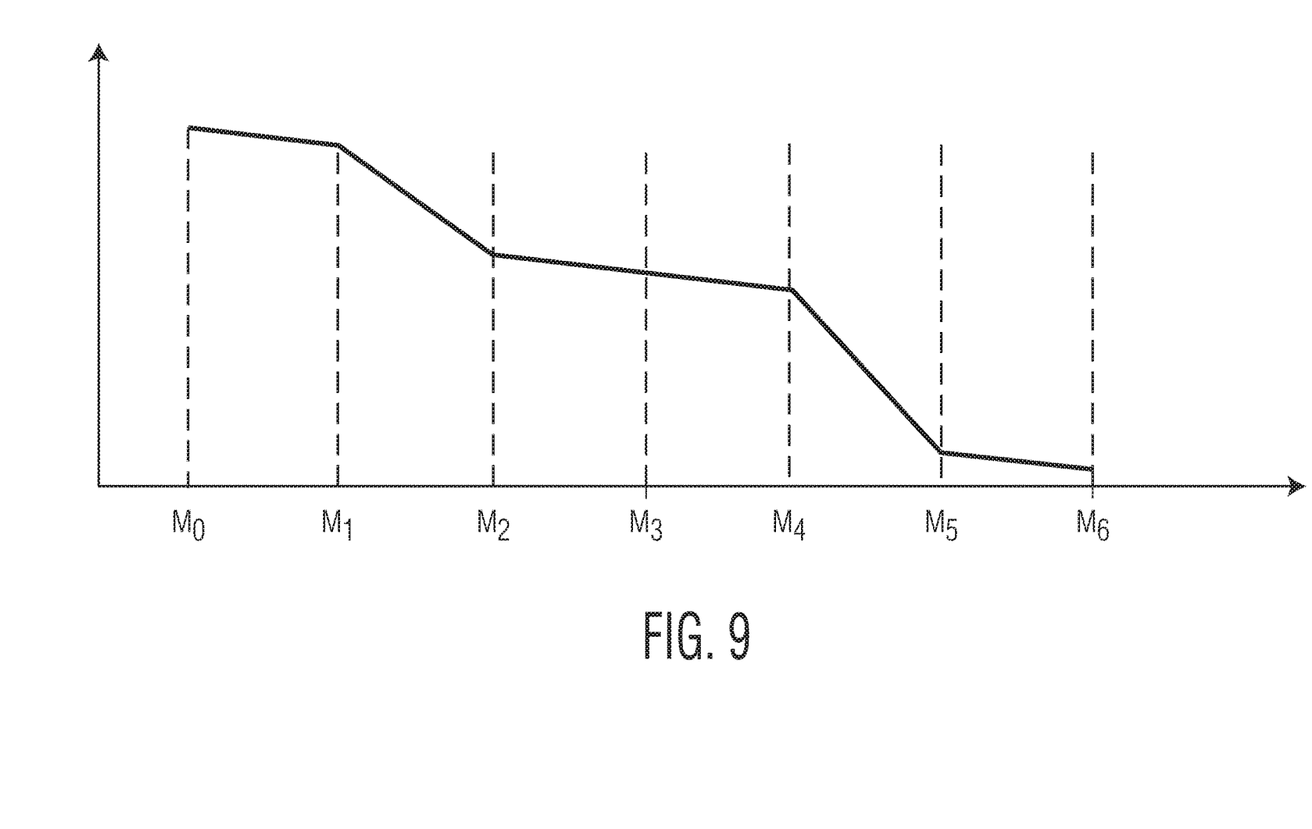

FIGS. 7, 8 and 9 present an example set of substance detection device elements configured to detect a substance based on a set of sensor output signals. These elements in various embodiments are apportioned between either an integration circuit (not shown), a detection circuit (not shown), a substance loss circuit (not shown), and/or a flow rate circuit (not shown).

To begin, define a section 702 as the part of the membrane from the previous sensor area to the end of the next sensor area. Sensors 704 are numbered from 0 to N.

Each sensor at position $x_k$ does a measurement $M(x_k,t)$, where:

$$M(x_k,t) = \phi(x_k,t) + S(x_k,t)$$

with $\phi(x,t)$ the fluid signal, and $S(x,t)$ the particle signal. At h system entry, both the fluid signal and the particle signal start at 0 and end at 0, i.e. the time integral becomes constant after a finite time $T_{int}$.

The fluid and particles are moving at velocity $v_f$ and $v_p$, and transit from the entrance of a section to the exit of a section in a time $T_f$ and $T_p$. Fluid travels faster than particles. The fluid signal at the exit of a section is equal to the fluid signal that entered a section $T_f$ time earlier. After the initial (dry→wet) transient, the fluid signal is constant.

In each section, particles are "lost" at a rate proportional to the particle signal $$L(x,t) = \alpha \cdot S(x,t)$$

The loss rate factor $\alpha$ is constant over all sections.

Where a test line is present, particles are "bound" at a rate proportional to the particle signal $$B(x,t) = \beta(x) \cdot S(x,t)$$

The binding rate factor $\beta(x)$ depends on the test line type and position and is constant over time.

The measurement at the exit of a section is given by:

$$M(x_k, t) = \varphi + S(x_k, t) = \varphi + S(x_{k-1}, t - T_p) - \int_{t-T_p}^{t} \int_{x_{k-1}}^{x_k} \alpha \cdot S(x,t) dx dt - \int_{t-T_p}^{t} \int_{x_{k-1}}^{x_k} \beta(x) \cdot S(x,t) dx dt$$

$$M(x_k, t) = \varphi + S(x_{k-1}, t - T_p) - \alpha \int_{t-T_p}^{t} \int_{x_{k-1}}^{x_k} S(x,t) dx dt -$$

-continued $$\int_{x_{k-1}}^{x_k} \beta(x) \int_{t-T_p}^{t} S(x,t) dt dx$$

This expression is approximated by $$M(x_k,t) = \phi + S(x_{k-1}, t-T_p) - a \cdot S(x_{k-1}, t-T_p) - b_k \cdot S(x_{k-1}, t-T_p)$$
$$= \omega + (1-a-b_k) \cdot S(x_{k-1}, t-T_p)$$

where the factor $b_k$ depends on the presence of a test or control line in the section. After the particle and fluid transitions, the situation for each measurement is stable. The loss factor a is typically kept as small as possible (<0.1%), and is a known property of the membrane, the binding factor b is optimized to be as large as possible (>5%), and depends on the result of the test (positive or negative) and the concentration of the target molecule in the fluid.

Two cases are now observed:

If no binding occurs (no test line or test negative), the measurement at exit of a section is $$M(x_k,t) = \phi + (1-a) \cdot S(x_{k-1}, t-T_p)$$

If binding occurs (test positive, or control line is in section)

$$M(x_k,t) = \phi + (1-a-b_k) \cdot S(x_{k-1}, t-T_p)$$

As particles accumulate over time, until no more particles or fluid are present at the input, we can calculate the time integral to get this recursive equation.

$$M_i(x_k) = \int_T \varphi + (1-a-b_k) \cdot \int_T S(x_{k-1}, t) = \varphi_i + (1+a-b_k) \cdot S_i(x_{k-1})$$

At each section exit:

$$M_i(x_k) = \varphi_i + \left( \prod_k (1-a-b_k) \right) S_i(x_0)$$

Calculating the difference with $M_i(x_0) = \phi_i + S_i(x_0)$ yields:

$$\Delta_k = M_i(x_0) - M_i(x_k) = \left[ 1 - \left( \prod_k (1-a-b_k) \right) \right] S_i(x_0)$$

The ratio of a sequence of $\Delta_k$ is $$\frac{\Delta_{k+1}}{\Delta_k} = \frac{1 - \left( \prod_{k-1} (1-a-b_k) \right)}{1 - \left( \prod_k (1-a-b_k) \right)}$$

Since the value a is known, calculate the bk if we have a sequence of sections with and without binding.

In an example embodiment, the sequence of measurement will follow a power law with two different slopes: a nearly flat (slow) decay where only losses occur, and a high (fast) decay where binding occurs. The measurement is affected by the uncertainty (noise) of parameter a, and not by the position of the binding sites.

Note that in various examples, one or more of the circuits coupled to the substance detection device 102 can be wholly or partially embodied in software, either operating on a computer, embedded in firmware, in a non-transient machine-readable storage medium, or operating remotely over a network.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A substance detection device, comprising:
   a substrate configured to carry a substance;
   wherein the substrate has a length and a substance loss along the length of the substrate;
   a test region coupled to the substrate and configured to bond to at least a portion of the substance;
   a sensor coupled to the substrate at a fixed location along the length and having a sensing signal output;
   an integration circuit coupled to the sensor and configured to integrate, over a time interval, a signal from the sensing signal output; and
   a detection circuit coupled to the integration circuit and configured to output a substance detected signal if the integrated sensing signal output signal deviates from the substance loss corresponding to the fixed sensor location.

2. The device of claim 1:
   wherein the detection circuit is configured to output the substance detected signal if the integrated sensing signal output signal is either greater than or less than the substance loss corresponding to the fixed sensor location.

3. The device of claim 1:
   wherein the substance loss is either a uniform per unit length or variable substance loss.

4. The device of claim 1:
   wherein at the fixed location along the length, the test region is not located directly over the sensor.

5. The device of claim 1:
   wherein the sensor is a capacitive sensor.

6. The device of claim 1:
   wherein the substance is at least one of: a target molecule; a control molecule; a conjugate molecule, a particle, DNA, a protein, an enzyme, a peptide, a small molecules or a hormone.

7. The device of claim 1:
   wherein the substance is carried by at least one of: an analyte or biological fluid.

8. The device of claim 1:
   wherein the test region includes at least one of: an antibody, a sensitive region, or a biomarker.

9. The device of claim 1:
   wherein the substance detected signal is a pregnancy detected signal.

10. The device of claim 1:
    wherein the sensor is included in a set of sensors 106, each having a sensing signal output, and aligned in a row along the length of the substrate at a corresponding set of fixed sensor locations;
    wherein the integration circuit is coupled to the set of sensors and is configured to integrate, over the time interval, signals from the sensing signal outputs; and wherein the detection circuit is configured to output the substance detected signal if at least one of the integrated sensing signal output signals deviates from a corresponding substance loss at that fixed sensor location.

11. The device of claim 1:
wherein the substrate is a membrane having a porosity between 66% and 98% by volume.

12. The device of claim 1:
wherein the sensor includes a set of electrodes separated from the substrate by an electrical insulator.

13. The device of claim 1:
wherein the sensor is included in a set of sensors, each having a sensing signal output, and aligned in a row along the length of the substrate at a corresponding set of fixed sensor locations; and
further comprising a substance loss circuit configured to compare the set of sensing signal outputs to calculate the substance loss.

14. The device of claim 1:
wherein the sensor is included in a set of sensors, each having a sensing signal output, and aligned in a row along the length of the substrate at a corresponding set of fixed sensor locations; and
further comprising a flow rate circuit configured to determine a volume flow rate along the substrate by comparing the set of sensing signal outputs.

15. The device of claim 1:
wherein the substrate configured to carry a second substance;
wherein the substrate has a second substance loss with respect to the second substance;
further comprising,
a control region coupled to the substrate and configured to bond to at least a portion of the second substance; and
a second sensor coupled to the substrate at a second fixed location along the length and having a second sensing signal output;
wherein the integration circuit is coupled to the second sensor and is configured to integrate, over a time interval, a signal from the second sensing signal output; and
wherein the detection circuit is configured to output a second substance detected signal if the second integrated sensing signal output signal deviates from a second substance loss corresponding to the second fixed sensor location.

16. A pregnancy test device comprising:
a substrate configured to carry a substance;
wherein the substrate has a length and a substance loss along the length of the substrate;
a test region coupled to the substrate and configured to bond to at least a portion of the substance;
a sensor coupled to the substrate at a fixed location along the length and having a sensing signal output;
an integration circuit coupled to the sensor and configured to integrate, over a time interval, a signal from the sensing signal output; and
a detection circuit coupled to the integration circuit and configured to output a pregnancy detected signal if the integrated sensing signal output signal deviates from the substance loss corresponding to the fixed sensor location.

\* \* \* \* \*